United States Patent [19]

Lees

[11] Patent Number: 4,937,067

[45] Date of Patent: * Jun. 26, 1990

[54] METHOD AND MEANS FOR DETECTION OF ADRENAL METABOLIC ACTIVITY

[75] Inventor: Robert S. Lees, Brookline, Mass.

[73] Assignee: Massachusetts Institute of Technology, Cambridge, Mass.

[ * ] Notice: The portion of the term of this patent subsequent to Mar. 3, 2004 has been disclaimed.

[21] Appl. No.: 227,449

[22] Filed: Aug. 2, 1988

Related U.S. Application Data

[63] Continuation of Ser. No. 681,245, Dec. 13, 1984, abandoned.

[51] Int. Cl.$^5$ .............................................. A61K 49/02
[52] U.S. Cl. ........................................ 424/1.1; 424/9; 128/659
[58] Field of Search ..................... 424/1.1, 9; 436/804; 534/14; 128/659

[56] References Cited

U.S. PATENT DOCUMENTS

| | | | |
|---|---|---|---|
| 4,215,045 | 7/1980 | Knapp | 424/1.1 |
| 4,323,546 | 4/1982 | Crockford et al. | 534/14 |
| 4,421,735 | 12/1983 | Haber et al. | 424/1.1 |
| 4,490,350 | 12/1984 | Zolle | 424/1.1 |
| 4,528,177 | 7/1985 | Molloy et al. | 424/9 |
| 4,647,445 | 3/1987 | Lees | 424/1.1 |

OTHER PUBLICATIONS

Kovanen et al., *J. Biol. Chem.*, vol. 254, No. 12, 1979, pp. 5498–5505.

Counsell et al., *Biochim. Biophys. ACTA*, 750, 1983, pp. 497–503.

Roheim et al., *Biochim. Biophys. ACTA*, 248, 1971, pp. 315–329.

B. Shapiro et al., *Clinical Experience With $^{75}Se$ Selenomethylcholesterol Adrenol Imaging* (1981) 15, 19–27.

Richard J. Blair et al., *Radiolabeled Cholesterol as an Adrenal Scanning Agent*, 176–182.

William H. Beierwaltes et al., *Adrenal Imaging Agents: Rationale, Synthesis, Formulation and Metabolism*, vol. VIII, No. 1 (1978).

D. Roger Illingsworth, *Adrenal Cortical Function in Homozygous Familial Hypercholesterolemia*, vol. 30, No. 11 (Nov.), 1983.

Ann M. Lees and Robert S. Lees, *Low Density Lipoprotein Degredation by Mononuclear Cells from Normal and Dyslipoproteinemic Subjects*, vol. 80, pp. 5098–5102, Aug. 1983, Medical Sciences.

Dr. Jonathan L. Isaacson, 1984 *Abstract Form For Scientific Papers and Scientific Exhibits Society of Nuclear Medicine* 31st Annual Meeting, Los Angeles, CA, June 5–8, 1984.

*Primary Examiner*—Howard J. Locker
*Assistant Examiner*—J. E. Thomas
*Attorney, Agent, or Firm*—Nutter, McClennen & Fish

[57] ABSTRACT

The metabolic activity of the adrenal gland can be monitored by intravenously injecting an infusate composed of low density lipoproteins labelled with a radioisotope that is suitable for extracorporeal imaging and subsequently measuring the intensity of radioisotope accumulation in organs of the body. By monitoring the accumulation at the sites of the adrenal glands, the metabolic activity can be localized and the level of activity can be assessed.

3 Claims, 2 Drawing Sheets

LDL RABBIT -- #07
21 HOURS POST INJ

1 MO POST BALLOON
INJURY

METHOD AND MEANS FOR DETECTION OF ADRENAL METABOLIC ACTIVITY

This application is a continuation of application Ser. No. 681,245, filed Dec. 13, 1984, now abandoned.

CROSS REFERENCE TO RELATED APPLICATIONS

This application is related to U.S. application Ser. No. 594,244, filed Mar. 28, 1984, now U.S. Pat. No. 4,647,445, titled IMPROVED RADIOLABELLED LIPOPROTEINS AND METHOD FOR MAKING SAME, the disclosures of which are incorporated by reference herein and is a continuation of U.S. application Ser. No. 681,245, now abandoned.

FIELD OF THE INVENTION

This invention relates to a method and means for detection of adrenal metabolic activity, and more specifically, to a method and means for extracorporeal imaging of adrenal activity.

BACKGROUND OF THE INVENTION

The adrenal glands are two secretory organs located on top of the kidneys. Each gland consists of two parts, the cortex and the medulla, which have independent functions. The adrenal cortex secretes numerous steroids, e.g. corticoids and androgens. These steroids are involved in various metabolic processes throughout the body and are essential for homeostasis, the maintenance of the internal environment of the body. For example, glucocorticoids such as cortisol, play a role in carbohydrate and protein metabolism, while mineralocorticoids, such as aldosterone, function in electrolyte and water metabolism. The androgens supplement the hormones secreted by the gonads.

Defects in adrenal cortical function result in severe metabolic disturbances that affect the entire body. If the adrenals were removed, the subject would die within a short period, unless appropriate medications were administered. Some tumors, either benign or cancerous, in one or both of the adrenal glands cause increased androgen synthesis. The result is masculinization, independent of the sex or age of the affected patient. Other tumors cause selective increases in glucocorticoid synthesis or in mineralocorticoid synthesis, resulting in accumulation of fat, hyperglycemia, muscle weakness, and decreased immunity to infection, as well as other symptoms.

Typical therapy is aimed at removal or destruction of the hyperfunctioning tissue. For this reason, it is necessary to identify and localize the malfunction in one or both of the adrenal glands. Of special interest is the diagnosis of these disorders using non-invasive techniques. Heretofore, extracorporeal imaging of the adrenal glands has been attempted using radiolabelled cholesterol and radiolabelled cholesterol derivatives as probes.

These probes were chosen because cholesterol is a principal precursor in steroid biosynthesis. While steroids can be synthesized de novo in the adrenal glands from a simple two-carbon acetate precursor, it is believed that the majority of steroids may be synthesized instead from cholesterol derived from low density lipoproteins which circulate in the blood stream.

Beierwaltes and his colleagues used $^{131}$I-iodocholesterol and other iodinated cholesterol-like compounds to visualize adrenal uptake in animals by extracorporeal imaging (Beierwaltes et al., *Seminars in Nuclear Medicine VIII*: 5, 1978; and Blair et al., *Journal of Nuclear Medicine* 12: 176, 1971). In experiments in animals, these researchers found that, shortly after injection, uptake of cholesterol was relatively uniform throughout all tissues, but that after one or two days, cholesterol was retained to a greater extent in the adrenal glands. However, their attempts to image the human adrenal were not as successful. They reported evidence of imaging of the human adrenal glands using a radiolabelled iodocholesterol derivative only at 5–7 days after injection.

Shapiro et al. have also investigated the usefulness of extracorporeal imaging with $^{75}$Se-selenomethylcholesterol for studying human adrenal pathologies (*Clinical Endocrinology* 15: 19, 1981). Using this radiolabelled cholesterol probe, they found that the adrenal gland could be imaged. They also found that this probe could be used to diagnose some, but not all adrenal pathologies.

While Shapiro's probe permits imaging of the human adrenal glands, it requires seven to ten days after injection of the probe before the cholesterol concentrates in the adrenal glands to a sufficient extent for the glands to be visualized by extracorporeal imaging. This lengthy time delay increases the radioactive dose required to provide a suitable image, and therefore interferes with its effectiveness as an experimental and clinical diagnostic tool.

Thus both Beierwaltes' and Shapiro's methods described above demonstrate the limitations of radiolabelled cholesterol for use as an adrenal imaging agent. An ideal imaging agent would quickly concentrate in the adrenal glands relative to other organs, and would therefore permit imaging of the adrenals shortly after injection of the radiolabelled imaging agent. It would also expose the subject to a minimal radioactive dose.

SUMMARY OF THE INVENTION

Accordingly, the present invention aims to provide an improved method and means for detection of adrenal metabolic activity that is non-invasive and causes little trauma to the patient.

It is another object of the invention to provide a method and means for detection of adrenal metabolic activity that is sensitive, relatively rapid and efficient and exposes the subject to a relatively small radioactive dose.

Still another object of the present invention is to provide a method and means for assessing the extent and location of adrenal metabolic activity.

Briefly, my invention resides in the discovery that adrenal uptake of low density lipoproteins can be monitored extracorporeally using lipoproteins radiolabelled with technetium-99m, and that this uptake corresponds to the degree of adrenal metabolic activity. Because technetium-99m is a strong gamma radiation emitter, uptake of the radiolabelled LDL in any tissue can be monitored easily by extracorporeal imaging. Thus by measuring the intensity of gamma radiation from the adrenal gland, the level of metabolic activity of each gland can be quantified.

The method operates relatively quickly. Thus, imaging in man can be performed within one day after intravenous introduction of the radiolabelled lipoproteins. It appears that the lengthier time delay encountered when a cholesterol probe is employed can be attributed to the body mechanisms involved in tissue uptake and resecretion of intravenously administered cholesterol. Cholesterol infused into the bloodstream is not in a form which can be directly utilized in the body. It is taken up by unknown tissues and slowly incorporated into lipoproteins, which are then secreted into the bloodstream. Only lipoprotein-bound cholesterol is transported through the body for distribution and absorption by target organs. Accordingly, we believe that radiolabelled LDL probes will be absorbed by the target organs faster than their cholesterol counterparts, thus materially reducing the amount of time after injection required for obtaining suitable extracorporeal images.

To accomplish this $^{99m}$Tc-LDL is injected intravenously into the subject and 4–24 hours later, the subject is scanned with a standard gamma radiation detector. The sites of metabolic uptake of interest, such as the adrenal gland, are thus located and the extent of metabolic activity thereof can be assessed from the images produced by the detector.

Thus, our procedure can be performed simply and non-invasively, and can be used to evaluate both the extent and localization of adrenal activity, i.e. adrenal insufficiency, hyperactivity, or lateralization thereof. The procedure has potential for clinical diagnosis of adrenal dysfunctions, evaluation of therapy, and experimental investigation of adrenal function. We have shown in two human subjects that the adrenal glands may be in imaged in 24 hours after intravenous injection of $^{99m}$Tc-LDL.

BRIEF DESCRIPTION OF THE FIGURES

FIG. 3A depicts a posterior scintigram of a human abdomen taken 24 hours post-injection of 10–20 mCi $^{99m}$Tc-LDL.

FIG. 3B depicts another posterior scintigram of the same subject of FIG. 3B, taken through a 3 mm pinhole camera and represents a close-up of the region of the adrenal and kidney.

DETAILED DESCRIPTION OF THE PREFERRED EMBODIMENT

PREPARATION OF THE RADIOLABELLED PROBE

Low density lipoproteins (LDL) are isolated from human sera and radiolabelled according to the method described in my pending U.S. patent application Ser. No. 594,244, now U.S. Pat. No. 4,647,445, titled IMPROVED RADIOLABELLED LIPOPROTEINS AND METHODS FOR MAKING SAME, filed Mar. 28, 1984, now U.S. Pat. No. 4,647,445. Briefly, low density lipoproteins (LDL), isolated from normal human plasma, are coupled with a technetium isotope, $^{99m}$Tc, by the following procedure. 50 mCi $^{99m}$Tc (in the form of TcO$_4$-) in a 0.5 ml aqueous solution, is added to 2–6 mg LDL in 0.5 ml of 0.2M sodium bicarbonate, pH 8, and mixed throughly for ten minutes at room temperature. The pH is raised to 8–9, if necessary, with 0.25M sodium hydroxide, and the mixture is reduced by the addition of 10 mg sodium dithionite (57.5 umoles) freshly dissolved in 0.5 ml distilled water. The mixture is gently stirred for 30 minutes at room temperature.

The radiolabelled LDL fraction is separated from denatured or aggregated LDL, uncoupled technetium, and sodium dithionite by molecular sieve chromatography. A 2×5 cm column of Sephadex G50M equilibrated with a bicarbonate-EDTA buffer [containing 0.2M sodium bicarbonate, pH 8, and 0.01M disodium ethylene diamine tetraacetic acid (EDTA)], is suitable for a separation. The column is standardized with blue dextran and potassium iodide to determine the void volume and the column volume, respectively. The reaction mixture is applied to the column and bicarbonate-EDTA buffer is used to elute column fractions. The macromolecular radioactive peak that elutes at a position characteristic for LDL is isolated for use.

Alternatively, LDL can be labelled with technetium or other radioisotopes that are suited for extracorporeal imaging by covalently attaching a strong chelating agent to the lipoprotein. The radioisotope subsequently attaches to the chelating agent to form the radiolabelled lipoprotein complex. DTPA is known to chelate metals, including radioisotopes of technetium, indium, lead and mercury, and can be covalently attached to the lipoprotein.

IN VIVO DISTRIBUTION OF TC-LDL IN RABBITS

Figure 1:
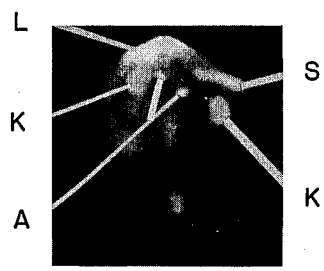
FIG. 1 depicts a representative anterior scintigram of a rabbit 16 hours after intravenous injection of 3 mCi $^{99m}$Tc-LDL.

Sixteen New Zealand White rabbits (2–3 kg) were injected intravenously with $^{99m}$Tc-LDL (4–8 mCi, 1.5 mg protein). Sixteen hours after injection, the rabbits were anesthetized and imaged anteriorly and posteriorly with a standard Anger-scintillation camera (Technicare 550) with a parallel-hole collimator. Imaging time was 10 minutes and approximately 300,000 counts were obtained during this time. A typical scintigram is shown in FIG. 1. Radioactivity accumulated in various organs, such as the adrenals (A), liver (L), kidneys (K), and spleen (S).

Eighteen hours post-injection, the rabbits were sacrificed, and the organs were removed, cleaned, weighed, and the radioactivity was counted. In the following table, the biodistribution of $^{99m}$Tc-LDL is expressed in percent of injected radioactivity per gram and per organ:

TABLE 1

Biodistribution of $^{99m}$Tc-LDL in the Rabbit

| Organ | Percent of Injected Radioactivity per Gram (mean ± S.E.M.) | per organ (mean ± S.E.M.) |
|---|---|---|
| Venous Blood | 0.03 ± 0.01 | — |
| Liver | 0.19 ± 0.02 | 21.1 ± 1.3 |
| Spleen | 0.22 ± 0.04 | 0.4 ± 0.1 |
| Adrenal (whole)* | 0.81 ± 0.19 | 0.2 ± 0.1 |
| (cortex)* | 0.92 ± 0.09 | 0.3 ± 0.1 |
| (medulla)* | 0.59 ± 0.06 | 0.1 ± 0.1 |
| Kidney (cortex) | 0.11 ± 0.02 | 2.9 ± 0.4 |
| (medulla) | 0.04 ± 0.01 | 0.9 ± 0.2 |
| Small Bowel | 0.01 ± 0.00 | 1.3 ± 0.2** |
| Large Bowel | 0.05 ± 0.01 | 2.3 ± 0.3** |
| Muscle | 0.002 ± 0.0 | 1.6 ± 0.3** |

TABLE 1-continued

Biodistribution of $^{99m}$Tc-LDL in the Rabbit

| Organ | Percent of Injected Radioactivity | |
|---|---|---|
| | per Gram (mean ± S.E.M.) | per organ (mean ± S.E.M.) |
| Aorta (thoracic) | 0.02 ± 0.00 | — |

*The entire adrenal gland was weighed and counted in 12 animals, while cortex and medulla were dissected out, weighed, and counted separately in 4 animals.
**Percent of the injected dose is expressed per 100 gm for small and large bowel, while that for muscle is expressed for body muscle mass, assumed to be 45% of body weight.

The intensity of the image visualized in FIG. 1 for each organ was found to be proportional to the radioactivity measured in the biodistribution study shown in Table 1. Biodistribution of $^{99m}$Tc-LDL demonstrated that 0.81±0.19% of the injected radioactivity was taken up per gram of whole adrenal gland. This uptake is compared with 0.19±0.02% per gram by liver, 0.22±0.04% per gram by spleen, and 0.11±0.02% per gram by kidney. Thus, even though the adrenal gland is smaller in size, the higher uptake enables it to be visualized in spite of the background levels in other organs.

Figure 2A:
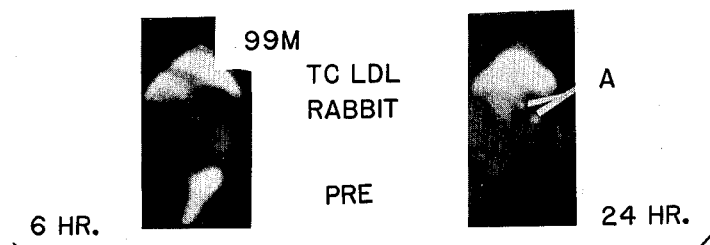
FIG. 2A depicts anterior scintigrams of another rabbit six and twenty-four hours, respectively, post-intravenous injection of 3 mCi $^{99m}$Tc-LDL, before treatment with dexamethasone, a drug which suppresses adrenal function.
Figure 2B:
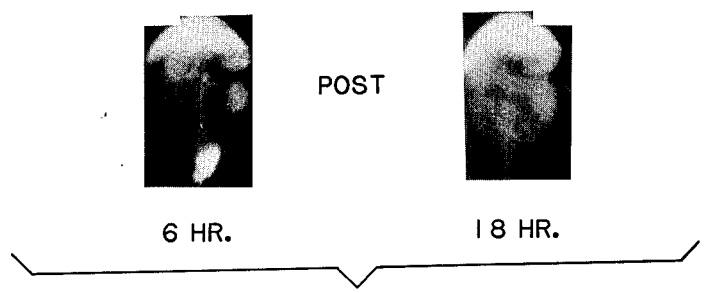
FIG. 2B depicts anterior scintigrams of the same rabbit after five days' treatment with dexamethasone, taken six and twenty-four hours post-injection of 3 mCi $^{99m}$Tc-LDL.

In separate experiments, additional rabbits were tested for adrenal activity before and after injection of dexamethasone, a drug which suppresses adrenal cortical function. The rabbits were first injected with 3-5 mCi $^{99m}$Tc-LDL and six and twenty-four hours later, the rabbits were anesthetized and imaged as described previously. The adrenal glands (A) were again well-visualized by the gamma scans, as shown in FIG. 2A. The rabbits were then given dexamethasone for five days to suppress adrenal cortical function. The degree of suppression was monitored by serum cortisol measurements. After five days, when $^{99m}$Tc-LDL was again injected intravenously into the rabbits, the adrenals could not be visualized six and 18 hours after injection. The rabbits were then sacrificed and the adrenals were removed, cleaned, weighed, and the radioactivity of each of the glands was counted. The counts in the adrenals were at background levels. These data indicate that $^{99m}$Tc-LDL can be used to monitor adrenal cortical activity.

Six human subjects were injected intravenously with 10-20 mCi $^{99m}$Tc-LDL and their abdomens were imaged with a gamma camera several times during the next 4-48 hours following injection. In four of the subjects who were not acutely ill, no accumulation of radioisotope was observed in the adrenal glands upon external imaging. In two subjects who had suffered an acute myocardial infarction one to two weeks previously, and whose adrenal function could confidently be considered above normal in response to this stress, the adrenal glands were visible on the external image at 24 hours.

Figures 3A, 3B:
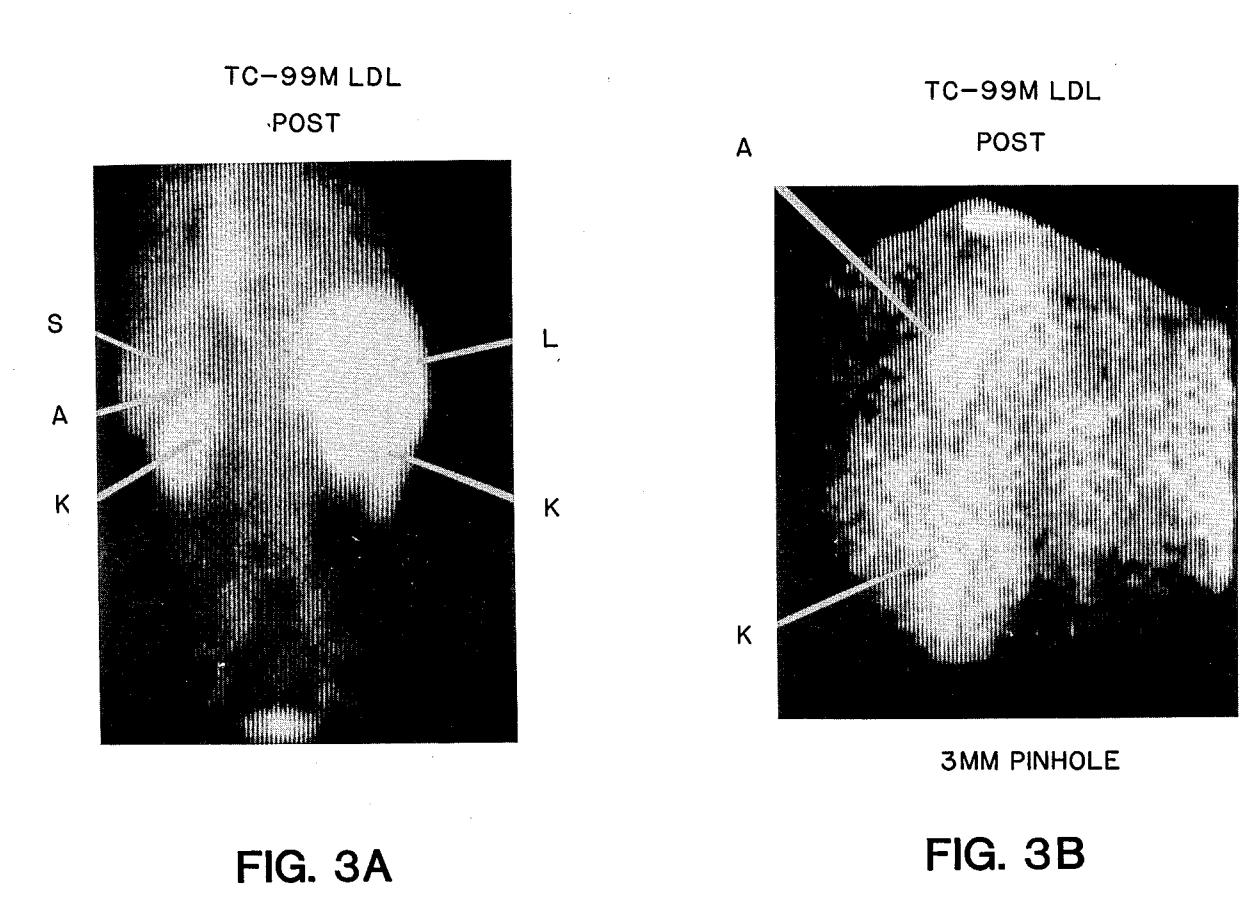

As shown in FIG. 3A, radioactivity acumulated in a number of organs of one of the latter subjects. These organs are identified as the adrenal (A), kidney (K), liver (L), and spleen (S). In this image, the liver camoflages uptake by the right kidney and right adrenal. FIG. 3B is a close-up view of the region of the left kidney (K) and adrenal gland (A). Thus, these experiments show that imaging of the human adrenal gland can be accomplished with radiolabelled low-density lipoproteins.

It can be seen from the foregoing description that technetium-labelled low-density lipoproteins are taken up by the adrenal glands and that this uptake can be monitored by extracorporeal imaging of the intact animal. Furthermore, this uptake correlates with adrenal metabolic activity, and should facilitate clinical assessment of adrenal suppression or hyperfunction. It is thus a useful diagnostic tool for clinical evaluation and experimental investigation of adrenal disorders and the treatment thereof.

It will thus be seen that the objects set forth above, among those made apparent from the preceding description, are efficiently obtained. Also, certain changes may be made in carrying out the above procedures without departing from the scope of the invention.

For example, instead of using technetium-labelled low-density lipoproteins, radiolabelled derivatives of low-density lipoprotein or of active amino acid sequences of the lipoprotein can be used. LDL has been demonstrated to bind to steroidogenic tissue through a high-affinity receptor. These receptors react with a specific region on the molecule rich in lysine and arginine residues. A radiolabelled probe consisting mainly of this receptor-binding region should be expected to provide a more specific agent for adrenal imaging. Also, reductive methylation of LDL has been shown to abolish this high-affinity receptor binding activity. Accordingly, radiolabelled, methylated LDL can be used under experimental research conditions to assess the effect of non-receptor-mediated binding on adrenal function.

Similarly, a lipoprotein molecule can be modified for more selective uptake by the adrenal gland, thus enhancing the quality of the resulting adrenal image by eliminating background uptake by other organs.

Accordingly, it is intended that the matter contained in the above description and shown in the accompanying figures be interpreted as illustrated and not in a limiting sense.

It is also to be understood that the following claims are intended to cover all the generic and specific features of the invention herein described. What is claimed as new and desired to be secured by the Letters Patent of the United States is:

1. A method for extracorporeal detection of metabolic activity in adrenal glands in rabbits and humans comprising the steps of:
    A. introducing low-density lipoproteins that are radiolabelled with technetium-99m into the bloodstream; and
    B. detecting uptake of the low-density lipoproteins that occurs at locations of the adrenal glands.

2. A method for extracorporeal detection of metabolic activity in adrenal glands in rabbits and humans comprising the steps of:
    A. preparing an infusate composed of low-density lipoproteins that are linked with technetium-99m;
    B. injecting the infusate into the bloodstream of a subject; and
    C. subsequently viewing the subject with radiation detecting means.

3. The method according to claim 2 including the further step of quantitating the intensity of the radiation at the sites of the adrenal glands.

* * * * *